United States Patent [19]

Gutniak et al.

[11] Patent Number: 5,700,775
[45] Date of Patent: Dec. 23, 1997

[54] METHOD AND TREATMENT COMPOSITION FOR DECREASING PATIENT TIME IN CATABOLIC STATE AFTER TRAUMATIC INJURY

[76] Inventors: Mark K. Gutniak, Hässelby Strandväg 26, S-165 65 Hässelby, Sweden; Thomas R. Coolidge, 181 Beebe Hill Rd., Falls Village, Conn. 06031; Robert R. Recker, 3309 S. 116th St., Omaha, Nebr. 68144; Fred W. Wagner, R.R. 1, Box 77B, Walton, Nebr. 68461

[21] Appl. No.: 410,353

[22] Filed: Mar. 24, 1995

[51] Int. Cl.$^6$ .......................... A61K 38/27; A61K 37/00
[52] U.S. Cl. ................................... 514/12; 514/21
[58] Field of Search ........................... 514/12, 21

[56] References Cited

U.S. PATENT DOCUMENTS

| | | | |
|---|---|---|---|
| 4,710,382 | 12/1987 | Recker | 424/108 |
| 4,801,456 | 1/1989 | Drengler | 514/12 |
| 4,870,054 | 9/1989 | Recker | 514/12 |
| 5,164,368 | 11/1992 | Recker | 514/12 |

OTHER PUBLICATIONS

Goodman and Gilman, eds, The Pharmacological Basis of Therapeutics, pp. 1448–1464, Sixth Edition (1984) MacMillan Publishing Co. F. Merad and R.C. Haynes, Androgens and Anabolic Steroids.

Roberto Valcavi et al., Cardiac Performance and Mass in Adults with Hypopituitarism: Effects of One Year of Growth Hormone Treatment, 1995, Rome, Italy, pp. 659–666.

Marie Degerblad et al., Potent Effect of Recombinant Growth Hormone on Bone Mineral Density and Body Composition in Adults with Panhypop8ituitarism, 1992, Stockholm, Sweden,pp. 387–393.

Richard F. Walker et al., Effects of Growth Hormone Releasing Peptides on Stimulated Growth Hormone Secretion in Old Rats, no date available,pp. 167–192.

*Primary Examiner*—Cecilia J. Tsang
*Assistant Examiner*—P. Lynn Touzeau
*Attorney, Agent, or Firm*—Zarley, McKee, Thomte, Voorhees & Sease

[57] ABSTRACT

A method of decreasing patient time in a catabolic state after a traumatic injury. The patient is administered systemically human growth hormone releasing factor or a biologically active analog of human growth hormone releasing factor. Administration in the case of voluntary traumatic injury such as surgery occurs just prior to commencing the surgery and thereafter continuing until recovery. In this way the time in a catabolic state is significantly decreased, and the patient moves more quickly to desired anabolic state necessary for recovery.

20 Claims, No Drawings

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 44 amino acids
        ( B ) TYPE: amino acid
        ( C ) STRANDEDNESS:
        ( D ) TOPOLOGY: Not Relevant ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

```
Tyr Ala Asp Ala Ile Phe Thr Asn Ser Tyr Arg Lys Val Leu Gly Gln
 1               5                  10                      15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
            35                  40
```

( 2 ) INFORMATION FOR SEQ ID NO:2:

( i ) SEQUENCE CHARACTERISTICS:

(A) LENGTH: 40 amino acids
(B) TYPE: amino acid
(C) STRANDEDNESS:
(D) TOPOLOGY: Not Relevant (i i) MOLECULE TYPE: protein (i i i) HYPOTHETICAL: NO (i v) ANTI-SENSE: NO (v) FRAGMENT TYPE: N-terminal (x i) SEQUENCE DESCRIPTION: SEQ ID NO:2:

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala
            35                  40

(2) INFORMATION FOR SEQ ID NO:3:

(i) SEQUENCE CHARACTERISTICS:
(A) LENGTH: 39 amino acids
(B) TYPE: amino acid
(C) STRANDEDNESS:
(D) TOPOLOGY: Not Relevant (i i) MOLECULE TYPE: protein (i i i) HYPOTHETICAL: NO (i v) ANTI-SENSE: NO (v) FRAGMENT TYPE: N-terminal (x i) SEQUENCE DESCRIPTION: SEQ ID NO:3:

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly
            35

(2) INFORMATION FOR SEQ ID NO:4:

(i) SEQUENCE CHARACTERISTICS:
(A) LENGTH: 32 amino acids
(B) TYPE: amino acid
(C) STRANDEDNESS:
(D) TOPOLOGY: Not Relevant (i i) MOLECULE TYPE: protein (i i i) HYPOTHETICAL: NO (i v) ANTI-SENSE: NO (v) FRAGMENT TYPE: N-terminal (x i) SEQUENCE DESCRIPTION: SEQ ID NO:4:

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

(2) INFORMATION FOR SEQ ID NO:5:

( i ) SEQUENCE CHARACTERISTICS:
    ( A ) LENGTH: 29 amino acids
    ( B ) TYPE: amino acid
    ( C ) STRANDEDNESS:
    ( D ) TOPOLOGY: Not Relevant ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:5:

```
Tyr Ala Asp Ala Ile Phe Thr Asn Ser Tyr Arg Lys Val Leu Gly Gln
1               5                   10                  15
Leu Ser Ala Arg Lys Leu Leu Gln Asp Ile Met Ser Arg
            20              25
```

( 2 ) INFORMATION FOR SEQ ID NO:6:

( i ) SEQUENCE CHARACTERISTICS:
        ( A ) LENGTH: 27 amino acids
        ( B ) TYPE: amino acid
        ( C ) STRANDEDNESS:
        ( D ) TOPOLOGY: Not Relevant ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:6:

```
Tyr Ala Asp Ala Ile Phe Thr Asn Ser Tyr Arg Lys Val Leu Gly Gln
1               5                   10                  15
Leu Ser Ala Arg Lys Leu Leu Gln Asp Ile Met
            20              25
```

( 2 ) INFORMATION FOR SEQ ID NO:7:

( i ) SEQUENCE CHARACTERISTICS:
        ( A ) LENGTH: 41 amino acids
        ( B ) TYPE: amino acid
        ( C ) STRANDEDNESS:
        ( D ) TOPOLOGY: Not Relevant ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:7:

```
Tyr Ala Asp Ala Ile Phe Thr Asn Ser Tyr Arg Lys Val Leu Gly Gln
1               5                   10                  15
Leu Ser Ala Arg Lys Leu Leu Gln Asp Ile Met Ser Arg Gln Gln Gly
            20              25                  30
Glu Ser Asn Gln Glu Arg Gly Ala Phe
            35              40
```

( 2 ) INFORMATION FOR SEQ ID NO:8:

( i ) SEQUENCE CHARACTERISTICS:
        ( A ) LENGTH: 42 amino acids (B) TYPE: amino acid
(C) STRANDEDNESS:
(D) TOPOLOGY: Not Relevant (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:8:

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Phe Gln
            35              40

METHOD AND TREATMENT COMPOSITION FOR DECREASING PATIENT TIME IN CATABOLIC STATE AFTER TRAUMATIC INJURY

BACKGROUND OF THE INVENTION

In the past 20 or so years, the physiology of pituitary function has become better understood. The pituitary gland secretes several hormones which in turn control secretion of other glands such as the adrenal, the thyroid, and the reproductive organs. In recent times, a series of pituitary releasing hormones have been discovered and characterized. The most recent of these is growth hormone releasing factor GRF(1-44)-$NH_2$. This discovery occurred in 1982 when two investigators independently, but almost simultaneously, reported the presence of a substance occurring in a pancreatic tumor which caused a clinical syndrome called acromegaly. In their respective journal articles, they reported that the tumors were found to contain a peptide consisting of 44 amino acids, which when purified and injected into animals or humans was found to stimulate the production of the several forms of growth hormone intensively, *Science*, Vol. 218, Nov. 5, 1982. pp. 585–87 and *Nature*, Vol. 300, Nov. 18, 1982, pp. 276–78. Recently, some researchers have successfully synthetically synthesized growth hormone releasing factor, and very recently it has been produced by genetic engineering procedures using bacterial cultures. For literature relating to synthetic production of growth hormone releasing factor, see Gelato, M. C. et al., 1983. "The Effects of Growth Hormone Releasing Factor in Man", *Journal of Clinical Endocrinology and Metab.* 57674.

Growth hormone releasing hormone factor is a peptide of 44 amino acids. There are analogs containing 27 to 44 amino acids. It is one of a group of peptides secreted by the hypothalamus, and it normally stimulates pituitary growth hormone release of the several isoforms of growth hormone and their respective control mechanisms or "feedback loops". It is important in normal growth and development during childhood.

Studies to date now suggest to us that growth hormone releasing factor initiates the cascade of endocrine hormone secretions, starting with the growth hormones, which serve to control the body's growth and maintenance functions. This can be referred to as the body's fundamental anabolic axis. It has been shown that, when deficient, this cascade or axis can be reactivated by growth hormone releasing factor in children with short stature for therapeutic purposes to increase growth velocity and also in the elderly or in adults generally with growth hormone deficiencies.

Recently it has been reported that GRF(1-44)-$NH_2$ may have some promise in the treatment of growth hormone deficiency (see *Journal of Clinical Endocrinology and Metab.* 59:1, 1984 and *Journal of Clinical Endocrinology and Metab.*, 58:1043, 1984). However, GRF(1-44)-$NH_2$ has not been marketed or suggested for any specific clinical disease treatment. It has been suggested as likely to be useful for testing pituitary function by using doses to stimulate pituitary secretion of growth hormone. The theory being that in the event it does not so stimulate, one knows that the pituitary gland is not functioning properly. However, when used to test pituitary function, GRF(1-44)-$NH_2$ is administered intravenously by a single bolus injection, and blood levels of growth hormone are measured in serum specimens obtained at approximately half hour intervals for four hours. If growth hormone levels fail to rise, then the presumption is made that the pituitary gland is incapable of secreting growth hormone. This is a single dose for diagnostic purposes, not a periodic and regular treatment pattern.

In two patents by one of the joint inventors herein, namely U.S. Pat. No. 4,870,054, issued Sep. 26, 1989, and U.S. Pat. No. 5,164,368, issued Nov. 17, 1992, growth hormone releasing factor, either alone or in combination with parathyroid hormone, is used for treatment of osteoporosis, especially postmenopausal osteoporosis. Continuing work of Dr. Recker and others has now discovered additional useful treatments with growth hormone releasing factor and its analogs. These additional treatments include new pre and post surgical trauma treatment that provides significantly enhanced patient recovery.

It has also been reported recently that the year-long application of growth hormone to growth hormone deficient adults will materially improve cardiac and cardiac muscle function (See *Journal of Clinical Endocrinology and Metab.* 80.2 P.659, 1995).

Trauma represents a large part of clinical medicine today. Elective surgery is the most common of all trauma. The injury caused by most surgical treatment leads to alterations in body metabolism that have implication for the recovery after surgery.

It has been more than half a century since Sir David Cuthbertson introduced the concept of ebb and flow phase of metabolism after physical injury. The "ebb" phase is characterized by a general fuel mobilization which lasts approximately 24 hours. This gradually shifts into the "flow phase", dominated by catabolism, which in turn slowly changes into anabolism and recovery.

The "ebb phase" is dominated by rapid mobilization of carbohydrates and fat. Glucose is released from stores of glycogen in the liver, while free fatty acids and glycerol are mobilized from adipose tissue. This response has been considered to be mediated mainly by release of stress hormones in response to trauma. However, energy expenditure is low in relation to the large amount of fuels available during this early period after trauma. If death does not occur due to massive blood loss or injury of vital organs, the "ebb phase" merges into the flow or "catabolic" phase, normally within 12–24 hours after the injury. During the "flow phase", energy expenditure is elevated and accompanied by an increased breakdown of body tissues. The duration of this period is more variable, and depends primarily on the severity of the injury. In order for the organisms to recover, the state of catabolism has to gradually shift into an anabolic or "convalescence" period resulting in partial or total recovery. This we have found requires stimulation and reactivation of the anabolic endocrine cascade which can be accomplished with the application of GRF(1-44)-$NH_2$ as described herein.

The development of hyperglycemia is the earliest reported change in carbohydrate metabolism following trauma. The degree of hyperglycemia found post-traumatically has been shown to be correlated to the severity of injury. There is an increase in hepatic glucose production, caused by increased liver glycogen breakdown as well as new glucose formation known as gluconeogenesis. The hyperglycemia is also accompanied by a reduction in metabolic clearance rate of glucose. In addition, the respiratory quotient is low, indicating an increased utilization of fat relative to that of carbohydrate. These changes in metabolism will ensure the glucose supply to glucose dependent tissues such as the brain, red blood cells and the renal medulla.

The net effect of trauma on protein metabolism is the development of catabolism, rendering losses of body nitrogen balance. Since skeletal muscle contains approximately 40% of the total amount of protein in man, the bulk of proteolysis occurs in this organ. The net losses of protein after trauma are due to a reduced protein synthetic rate and an increase in protein breakdown. The liberation of free amino acids from protein after injury constitutes an important source for gluconeogenesis, acute-phase protein formation, as well as protein synthesis in immune competent cells. Marked or sustained losses of muscular protein will have a negative effect on muscle function, increase the susceptibility to complications and the risk of impaired wound healing. Thus, postoperative fatigue is positively correlated to loss of weight following surgery, and risk of postoperative thromboembolism increase with reduced muscle function and immobilization. Consequently, considerable efforts have been made to minimize the catabolism of proteins after injury.

It can therefore be seen that if there were a method of rapidly decreasing the time a patient is in a catabolic state, or in other words, shortening the time from trauma to the patient's conversion to an anabolic state, this may well save the lives of many patients and probably improve the long term prognosis of patients after traumatic injury. For example, a change even locally from catabolic to anabolic state is extremely important where there has been a heart attack and the heart muscles are in jeopardy and prone to degradation during the catabolic condition. This also can be extremely important in other major traumas such as burn injuries, multiple fractures such as from car accidents, and in situations where there have been high fevers, infections, septic shock, etc. Hastening the change from catabolic to anabolic state and strengthening the anabolic effect of body repair mechanisms would be useful in nearly all traumatic injury cases, regardless of the cause of the traumatic injury, whether it be voluntary, such as during elective surgery, or physical trauma caused by accident.

Accordingly, a primary objective of the present invention is to provide a method of treatment which hastens the change from catabolic to anabolic state after a human patient's traumatic injury.

Another objective of the present invention is to provide a method of treatment for traumatic injuries which uses human growth hormone releasing factor or biologically acceptable analogs thereof either alone or in combination with other actives to synergistically hasten patient conversion from a catabolic state to an anabolic state.

Another objective of the present invention is to provide a method of successfully administering GRF(1-44)-NH$_2$ or biologically acceptable analogs thereof, either alone or concurrently with other actives to reduce the traumatic injury risk to patients.

An even further objective of the present invention is to provide an injectable administration composition, by intravenous, intramuscular, subcutaneous, or any sustained release method, which accomplishes each of the above objectives.

The method and means of accomplishing all of the objectives here mentioned, as well as others, will become apparent from the description of the invention which follows.

SUMMARY OF THE INVENTION

By way of summary illustration only, this invention, which is set forth in more detail in the detailed description and in the claims, involves treatment by administering on a periodic and regular basis to patients who either have suffered traumatic injury, or are about to suffer traumatic injury during surgery, an effective amount of human growth hormone releasing factor or a biologically active analog of human growth hormone releasing factor. The administration, preferably by injectable, occurs for a time period sufficient to hasten the patient's change from a catabolic to an anabolic state. The administration may continue throughout the recovery period of the patient.

DETAILED DESCRIPTION OF THE INVENTION

As earlier explained, the existence of a catabolic state after traumatic injury is well known and results in energy expenditure and increased breakdown of body tissues in the duration of the period depending upon the severity of the injury. This catabolic state is coupled with biological changes such as hyperglycemia, and increase in hepatic glucose production and a reduction in metabolic clearance rate of glucose. When the patient's recovery begins, these changes, as well as others earlier outlined, decrease. There is increased protein production, etc. as wound healing and recovery continue. Obviously, the length of time that a patient is in a catabolic state increases the patient's risk since they are more susceptible to infections and many other diseases simply because of the reduced efficiency of other body systems such as the immune system.

GRF(1-44)-NH$_2$ is an attractive molecule for treatment of trauma injury because the molecule is relatively small and simple, and therefore can be effective in systemic absorption. It is small enough to be absorbed across mucous membranes and reach the circulation intact in relatively high concentration. Since it is necessary to give the growth hormone releasing factor repeatedly over a period of time after injury, administration by injection is preferred. Administration by techniques such as intramuscular, subcutaneous or intravenous administration is best in initial stages after trauma. It is also conceivable that growth hormone releasing factor may be given orally by pill or capsule, nasal insufflation, or by rectal or vaginal suppository, but to date no such non-injection methods have yet been developed for commercial use.

The time of administration of the human GRF(1-44)-NH$_2$ normally continues throughout the recovery period from the traumatic injury. As earlier mentioned, the preferred administration is by injection.

Dosage level for GRF will vary depending upon age, weight and size of the patient, but typically satisfactory results may be obtained when administered at levels within the range of 50 micrograms to 3,000 micrograms daily. If one knows that the patient is about to undergo traumatic injury such as by elective surgery, it is helpful to begin the administration just prior to surgery and continue it through the time of recovery, at least until the patient is clearly converted from the catabolic to the anabolic phase.

The time between catabolic and anabolic phase for patients after traumatic injury can even be further hastened where response to growth hormone releasing factor is augmented by the conjunctive application of pyridostigmine or other agents for the suppression of samatostatin such as argenine, certain beta blockers, and other agents. This augmentation can be accomplished with the application of from 30 mg. to 60 mg. of oral pyridostigmine given at least 30 minutes prior to injection with GRF. It is believed that this works because pyridostigmine suppresses samatostatin. Samatostatin is a growth hormone releasing suppresser. The growth hormone response to GRF is therefore intensified in normals when pyridostigmine or other samatostatin suppressing agents are administered.

It has been recently shown that the action of growth hormone releasing factor in releasing the several growth hormones and activating the anabolic axis can be enhanced by the use of a class of small peptides, and analogs thereof, as well and chemical mimics of these peptides, generally referred to as growth hormone releasing peptides (see *Growth Hormone II—Basic and Clinical Aspects*, Springer/Verlag, 1994, Pg. 167). While the mechanisms are not understood, these peptides, and their analogs and chemical mimics, tend to cause the release of at least one species of growth hormone and to suppress the effect of samatostatin. Accordingly, this invention includes the use of these agents separately, or in combination with growth hormone releasing factor or its analogs, to effect the release of the growth hormones to accomplish the anabolic benefits herein sought.

The action of GRF alone can be further augmented when it is given in combination with other agents such as androgenic sex steroids of which testosterone analogs are an example. A range dose of testosterone analogs would be from 5 mg. to 30 mg. per day.

With respect to growth hormone releasing factor GRF(1-44)-$NH_2$, it should be noted that biologically active analogs thereof may also be used. There are several analogs of GRF(1-44)-$NH_2$ which have biological activity, but are somewhat less potent. It is contemplated that those analogs which are biologically active may also be used in the treatment process of the invention. Generally, growth hormone releasing factor analogs in both the free acid and amide forms, containing from 1-27 to 1-44 may have similar activity. Hence, active analogs may be selected from the group consisting of GRF(1-44)-$NH_2$, GRF(1-44)-OH, GRF(1-40)-OH, GRF(1-40)-$NH_2$, GRF(1-32)-$NH_2$, GRF(1-39)-$NH_2$, GRF(1-40)-Phe-$NH_2$, GRF(1-40)-Phe-OH, GRF(1-40)-Phe-Gin-$NH_2$, GRF(1-29)-$NH_2$, and GRF(1-27)-$NH_2$.

The following example is set forth to provide a sample protocol for administration of human GRF(1-44)-$NH_2$ or its biologically active analogs in conjunction with traumatic injury to convert from catabolic to anabolic state.

EXAMPLE

A patient suffers multiple fractures and soft tissue injuries of the extremities and trunk (in an automobile accident). After admission to the hospital, the acute problems of airway obstruction and blood loss are controlled. Open reduction of fractures is performed as required and returned to intensive care unit for recovery after surgery. GRF injections might begin on the day following the management of the acute injuries at 500 micrograms once or twice daily for an indefinite period of time. There should be no adverse effects during the period required for recovery from the acute injury. Thus, the medication could be given continuously for up to 6 to 12 months in order to hasten recovery.

The injectable GRF could be combined with daily injections of short acting testosterone analog or long acting depo testosterone as necessary. The long acting variety will deliver testosterone to the circulation over a period of three or more weeks.

When in the above example a naturally occurring growth hormone releasing factor GRF(1-44)-$NH_2$ is replaced with biologically active analogs thereof, substantially similar results are obtained. In particular, the biologically active analogs of GRF(1-44)-$NH_2$ which can be used in the treatment process of this example are the following: GRF(1-44)-OH, GRF(1-40)-OH, GRF(1-40)-$NH_2$, GRF(1-32)-$NH_2$, GRF(1-39)-$NH_2$, GRF(1-40)-Phe-$NH_2$, GRF(1-40)-Phe-OH, GRF(1-40)-Phe-Gin-$NH_2$, GRF(1-29)-$NH_2$, and GRF(1-27)-$NH_2$.

---

What is claimed is:

1. A method of decreasing patient time in a catabolic state after traumatic injury, comprising:
    administering systemically to a patient commencing at a time from just before to just after a traumatic injury a catabolic state time reducing effective amount of human GRF(1-44)-NH$_2$ or a biologically active analog thereof, and further providing that a somatostatin inhibiting agent is administered prior to the administration of the GRF(1-44)-NH$_2$.

2. The method of claim 1 wherein administration of human GRF(1-44)-NH$_2$ continues throughout the period of recovery from said traumatic injury.

3. The method of claim 1 wherein administration of the GRF(1-44)-NH$_2$ is by injection.

4. The method of claim 1 wherein the dosage level of the GRF(1-44)-NH$_2$ is within the range of 50 micrograms to 3000 micrograms daily.

5. The method of claim 1 wherein the treating compound is a GRF analog.

6. The method of claim 5 wherein said analog is selected from the group consisting of all analogs of GRF (1-27 through 1-44), in both the free acid and amide forms, and including GRF(1-44)-OH, GRF(1-40)-OH, GRF(1-40)-NH$_2$, GRF(1-39)-NH$_2$, GRF(1-32)-NH$_2$, GRF(1-29)-NH$_2$ and GRF(1-27)-NH$_2$, as well as GRF(1-40)-Phe-NH$_2$, GRF(1-40)-Phe-OH, GRF(1-40)-Phe-Gin-NH$_2$.

7. The method of claim 1 wherein growth hormone releasing factor or its analogs are administered in combination with an effective amount of one or more growth hormone releasing peptides, or analogs or chemical mimics thereof.

8. The method of claim 1 wherein growth hormone releasing peptides, and analogs thereof, as well as chemical mimics of these peptides, are administered in an effective amount.

9. The method of claim 1 wherein administration is by a non-injectable delivery method.

10. The method of claim 9 wherein the method is by oral administration.

11. The method of claim 9 wherein administration is by nasal insufflation.

12. A method according to claim 1 wherein the somatostatin inhibiting agent is selected from the group consisting of pyridostigmine, arginine, and beta blockers.

13. A method according to claim 12 wherein the somatostatin inhibiting agent is pyridostigmine, wherein the pyridostigmine is orally administered at a dose of from between 30 mg and 60 mg at least 30 minutes prior to administering the GRF(1-44)-NH$_2$.

14. A method of decreasing patient time in a catabolic state after traumatic injury, comprising:
    administering systemically to a patient commencing at a time from just before to just after a traumatic injury a catabolic state time reducing effective amount of human GRF(1-44)-NH$_2$ or a biologically active analog thereof, wherein the GRF(1-44)-NH$_2$ is administered in combination with androgenic sex steroids.

15. A method according to claim 14 wherein the androgenic sex steroids are testosterone analogs.

16. A method according to claim 15 wherein the testosterone analogs are administered at a dose of from 5 mg/day to 30 mg/day.

17. A method according to claim 14 wherein a somatostatin inhibiting agent is administered at least 30 minutes before administering the GRF(1-44)-NH$_2$.

18. The method of claim 1 where administration is by a route selected from the group consisting of orally, nasally, rectally, vaginally, and parenterally.

19. A method of decreasing patient time in a catabolic state after traumatic injury, comprising:
    administering systemically to a patient commencing at a time from just before to just after a traumatic injury human GRF(1-44)-NH$_2$ or a biologically active analog thereof, wherein the dosage level of the GRF(1-44)-NH$_2$ is within the range of 50–3000 micrograms daily, and further providing that between 30–60 mg. of pyridostigmine is administered at least 30 minutes prior to the administration of the GRF(1-44)-NH$_2$.

20. A method of decreasing patient time in a catabolic state after traumatic injury, comprising:
    administering systemically to a patient commencing at a time from just before to just after a traumatic injury human GRF(1-44)-NH$_2$ or a biologically active analog thereof, wherein the dosage level of the GRF(1-44)-NH$_2$ is within the range of 50–3000 micrograms daily, and further providing that the GRF(1-44)-NH$_2$ is administered in combination with from about 5–30 mg/day of at least one testosterone analog.

* * * * *